(12) United States Patent
Meyer

(10) Patent No.: US 9,044,452 B2
(45) Date of Patent: *Jun. 2, 2015

(54) USE OF RESINIFERATOXIN (RTX) FOR PRODUCING AN AGENT FOR TREATING JOINT PAINS AND METHOD FOR APPLYING SAID AGENT

(75) Inventor: Dominik Meyer, Zurich (CH)

(73) Assignee: MESTEX AG, Zürich (CH)

( * ) Notice: Subject to any disclaimer, the term of this patent is extended or adjusted under 35 U.S.C. 154(b) by 414 days.

This patent is subject to a terminal disclaimer.

(21) Appl. No.: 12/755,994

(22) Filed: Apr. 7, 2010

(65) Prior Publication Data

US 2010/0196281 A1  Aug. 5, 2010

Related U.S. Application Data

(62) Division of application No. 11/722,779, filed as application No. PCT/CH2004/000756 on Dec. 28, 2004, now abandoned.

(51) Int. Cl.
*A61K 31/56* (2006.01)
*A61K 31/335* (2006.01)
*A61K 31/357* (2006.01)

(52) U.S. Cl.
CPC ................................... *A61K 31/357* (2013.01)

(58) Field of Classification Search
None
See application file for complete search history.

(56) References Cited

U.S. PATENT DOCUMENTS

| 4,939,149 A | 7/1990 | Blumberg |
| 4,997,853 A | 3/1991 | Bernstein |
| 2002/0115105 A1* | 8/2002 | Zhang et al. ................... 435/7.1 |
| 2003/0104085 A1 | 6/2003 | Yeomans |
| 2004/0047807 A1* | 3/2004 | Meyer ......................... 424/9.42 |

FOREIGN PATENT DOCUMENTS

| CA | 2001194 | | 12/1995 | | |
| CA | 2291796 A1 | | 12/1998 | | |
| CA | 2442049 A1 | | 10/2002 | | |
| CA | 2510181 A1 | | 7/2004 | | |
| WO | WO 90/14083 | * | 5/1990 | ........... | A61K 31/335 |
| WO | 98/40070 | | 9/1998 | | |
| WO | WO 02/058688 | * | 8/2002 | ............. | A61K 31/05 |
| WO | 2004/058286 | | 7/2004 | | |

OTHER PUBLICATIONS

Strickley (Pharm Res 21:201-230, 2004).*
Calvillo et al (Spine (Phila Pa 1976) 23(9):1069-1072, 1998—abstract only).*
Remington: The Science and Practice of Pharmacy; 20th Edition; Chapter 47: Controlled-Release Drug-Delivery Systems; The University of the Sciences in Philadelphia; 2000.
Karai, L., et al.: "Deletion of vanilloid receptor 1—expressing primary afferent neurons for pain control"; The Journal of Clinical Investigation, United States; vol. 113, No. 9; May 2004; pp. 1344-1352; XP-002333034.
Berge et al.; "Phamaceutical Salts"; Journal of Pharmaceutical Sciences; vol. 66, No. 1, Jan. 1977; pp. 1-19.
Sarpotdar et al.; "Percutaneous Absorption Enhancement by Nonionic Surfactants"; Drug Development and Industrial Pharmacy; Dekker, New York; 1986; pp. 1625-1647.

* cited by examiner

*Primary Examiner* — Craig Ricci
(74) *Attorney, Agent, or Firm* — Rankin, Hill & Clark LLP

(57) ABSTRACT

A method for treating a joint affected by pain that involves injecting an agent that includes resiniferatoxin (RTX) dissolved in a physiologically suitable solvent locally into the intracapsular region or the bursa of the joint affected by pain.

14 Claims, No Drawings

USE OF RESINIFERATOXIN (RTX) FOR PRODUCING AN AGENT FOR TREATING JOINT PAINS AND METHOD FOR APPLYING SAID AGENT

CROSS-REFERENCE TO RELATED APPLICATION

This application is a division of co-pending application Ser. No. 11/722,779, filed Nov. 27, 2007, which is a US National Stage of PCT/CH2004/000756, filed Dec. 28, 2004.

BACKGROUND OF INVENTION

The invention relates to the use of resiniferatoxin (RTX) for treating joint pains and, more particularly, to a method for treating joint pains that involves applying said agent in the intracapsular space or joint capsule of the joint.

Pain, emanating from joints, frequently has its origin in the area of the joint capsule or in the area of the bone in the vicinity of a joint. In this connection, many analogies may come into consideration, such as arthrotic or arthritic forms of a disease, mechanical or other irritation of bone surfaces in the vicinity of a joint, irritation or injury to the ligament structures of joints, infections, autoimmune processes, etc. In all cases, which are of interest within the scope of this invention, the resulting pain emanates from nociceptive nerve fibers in the region near the joint. Nociceptive fibers are also referred to as C fibers and A delta fibers. If an analgesic substance (such as a local anesthetic or morphine) is injected into a joint so diseased, the symptoms of the patient are alleviated. However, the substances, customary at the present time, act for only a limited period, so that the symptoms generally return.

In general, the following methods are used at the present time for the treatment of painful, diseased joints:
  physiotherapy/movement therapy
  systemic analgesic/antiphlogistic therapy (etc.)
  local analgesic/antiphlogistic methods (etc.)
  surgical methods
  arthroscopic: debridement, joint toilette, etc.
  open/mini-open joint replacement, joint reinforcement, etc.

A series of known substances for the treatment of painful, inflamed joints has already been proposed in the literature, especially
  osmic acid or radioactive substances, such as technetium 99, which lead to synoviorthesis,
  injection of local anesthetics, hyaluronic acid preparations (etc.)
  injection of antiphlogistic agents
  injection of contrasting agents for joint diagnosis
  joint flushing for joint toilette
  chemical, thermal, electrical or surgical ablation of the nerves, which look after the joints.

All previously used substances and methods lead to only a relatively brief or incomplete freedom from pain or cause lasting damage to the joint.

For example, the known method of synoviorthesis has the disadvantage of destroying the molecular structures, especially of denaturing the proteins, which act as initiators of inflammation in the process of arthritis and, partly also in the development of arthroses. Moreover, a fibrosis of the joint capsules is formed, which is less likely to become inflamed and accordingly also is less painful. At the same time, due to the fibrosis of the joint, which occurs during the synoviorthesis, the hyperemia, which is generally present and also to be treated, is decreased, resulting also in therapeutic benefit. However, the fibrotic scarring after synoviorthesis may lead to decreased mobility of the joint, as well as to a decreased production of synovial fluid and to a destruction of the joint cartilage. This undesirable fibrosis of the joint capsule should be avoided and only the sensitive innervation of the joint should be switched off.

The EP-B 0 998 288 of CAMPBELL discloses the use of capsaicin and analogues thereof (simultaneously or sequentially) with a local anesthetic. Local anesthetics are intended to prevent the burning pain during the injection of RTX. If the local anesthetics have an antagonistic effect with respect to capsaicins, the concentration of capsaicins, when used in combination with local anesthetics, must be higher than when capsaicin is used alone, in order to achieve the desired pain therapy. As side effects, capsaicins bring about hyperemia and inflammation reactions of the tissue.

U.S. Pat. No. 4,997,853 of BERNSTEIN discloses the use of capsaicin together with a local anesthetic having topical activity for the treatment of topical pain syndromes.

Admittedly, the use of capsaicins without local anesthetics is known for systemic use (intraperitoneal, subcutaneous, intravenous, etc. administration) or for regional use (epidural, intrathecal, transcutaneous administration or as a regionally selective nerve block), however, always in combination with general anesthesia of the experimental animals. However, it is a decisive disadvantage of a regional or systemic use that not only the affected region is treated, but also the asymptomatic, adjacent regions.

Admittedly, the use of capsaicins in the bladder (intravesical) without local anesthesia is also known. However, the agent is used here only topically and is not injected through a skin barrier.

BRIEF SUMMARY OF THE INVENTION

The invention is to provide a remedy. It is an object of the invention to make available an agent for the treatment of joint pain that includes resiniferatoxin (RTX) dissolved in a suitable solvent and a method for the local injection of this agent, which, for long-lasting analgesia, permanently damage the nerve ends, responsible for nociception, without endangering the structures remote from the joint.

DETAILED DESCRIPTION OF THE INVENTION

Surprisingly, the same or a better effect was achieved by using RTX alone (preferably with a special concentration), that is, without general anesthesia of the patient, then when general anesthesia was employed.

Pursuant to the invention, this objective is accomplished by using resiniferatoxin (RTX) for treating joint pain and, more particularly, by a method involving injecting resiniferatoxin (RTX) dissolved in a suitable solvent locally into the intracapsular region or the bursa of a joint affected by pain.

Surprisingly, it was found that one of the capsaicin analogs, namely resiniferatoxin (RTX), when applied locally, is effective at a far greater dilution (of the order of 1:1000) than is capsaicin, when it is used without a local anesthetic. There is no burning and also no inflammation of tissue. In particular, the local intraarticular injection of RTX by itself (at a very low concentration) has proven to be more effective than an injection together with a local anesthetic. Moreover, it is free of inflammation and pain. In particular, this preparation may be used without using ethanol, which otherwise is always necessary for the known intravesical administration. It is a further surprising advantage of the use without local or general anesthesia that, due to the injection, a warm, pleasant sensation sets in, which decisively supports combating pain. In this way, an amelioration of pain is achieved, which surpasses that of a combination with local anesthetics. This may also be explained by the antagonistic effect, which the local anesthetics have for vanilloid receptor agonists since they partially block the desired neurotoxic effect of vanilloids.

The inventive method consists therein that resiniferatoxin (RTX) is injected locally into a painful or diseased joint of the human or animal body. The RTX may be left there or, after a certain period of action, drawn off once again partly or completely. The RTX diffuses to the sensitive nerve endings, which innervate the region of the joint directly or indirectly, inhibits on damages this region predominately and, with that, leads to a decrease in the perception of joint pain.

Furthermore, it is a novel feature of this method that the joint capsule is used for concentrating the effect of the RTX on the place where the pain originates and, by these means, permits a higher concentration of RTX than would be possible without the protective joint capsule at the same concentration and compatibility and, at the same time, to look after the vascular, nerve and other structures in the vicinity of the joint. Accordingly, a long-term amelioration of the sensation of pain, emanating from the diseased disk-capsule-joint complex, is achieved by inhibiting or switching off the conduction. This method may be used preventatively or therapeutically.

The advantages of the inventive use of RTX and of the inventive method for the local injection of the RTX into the joint capsule, are the following:

- The pleasant, warm sensation during the injection without anesthesia has a decisive, supportive to effect on the desired action.
- The intra-articular injection of RTX for the analgesic treatment of joints leads largely to a preservation of the capsule-disk structures, of the synovia and of the cartilage bone structures and, with that, to maintaining the physiological relationships.
- The utilization of the joint capsule as a natural boundary for the distribution of the RTX.
- The development of action of the RTX does not depend on specific, neuronal epitopes other than the TRPV1 receptor.
- The method can be carried out by people, who are not specialists.
- The method can be carried out with a thin needle, even one that is not an arthroscopic needle.
- The method is not subject to the risk of infection, in contrast to the popular method of cortisone injection, which promotes local infections strongly, since cortisone inhibits the immune system locally.
- The method leads to a local, sensitive denervation, that is, to a switching off of the pain-conducting nerves.
- Expansion of the joint mobility by eliminating painful movement limitation in contrast to synoviorthosis, for which movement limitation results due to the capsule fibrosis that arises.
- Positive preparation for a later arthroplasty. Due to the sclerotizing action of RTX (on the one hand, as a result of a chemical, biological reaction and, on the other, due to the mechanicals stressing during the pain-free use of the joint), the bone, in the vicinity of the joint, develops a more advantageous structure for holding a prosthesis at a later time.
- No local fatty tissue absorption (lipolysis).
- No weakening of collagenous tendon/disk/capsule structures.

The invention is described in the following for use in man, the dosages given referring particularly to human applications. However, the invention is also suitable for the veterinary sector, in which dosages would have to be adapted depending on the bodyweight of the respective animal.

For a particular embodiment, the use of resiniferatoxin (RTX), without the simultaneous administration of further pharmacologically active substances, relates to the preparation of an agent for the treatment of local pain, especially of a) local wound pain after surgery in the form of a flushing solution for intraoperative application for an open or arthroscopic or endoscopic surgery, including liposuction;

b) local treatment of joint pain by intraarticular injection in the case of
  - chondrocalcinosis
  - ligamentary damage
  - meniscus lesion
  - cartilage damage
  - synovitis
  - arthrofibrosis
  - Sudeck's disease
  - necrosis of portions of a joint
  - neuropathic joint pain c) local treatment of bone pain after bone surgery by application on the bone, for example, after
  - iliac crest osteotomy
  - Hallux-Valgus correction d) treatment of bone pain by injection into the bone, especially in the case of necrosis of the head of the femur into the latter or into the body of a vertebra in the case of osteochondrosis;

e) local treatment of joint stiffness, especially in the case of arthrofibrosis or a frozen shoulder;

f) local treatment of muscle pain by intramuscular injection, especially in the case of a muscle tear, muscular soreness or spastic diseases, g) local injection into the painful meniscus if there is degeneration of or a tear in the meniscus;

h) treatment of back pain by injection into the intervertebral disk in the case of degeneration of or a tear in the intervertebral disk;

i) injection about a painful nerve, especially in the case of trigeminus neuralgia, neurinoma, Morton neurinoma, phantom pain or scar neurinoma;

j) treatment of toothache by local intradental or peridental administration, especially in the case of dental caries, all forms of toothache, before, during or after tooth extraction, before, during or after a tooth implanting, applied topically in the case of parodontitis, or applied topically in the case of an exposed neck of a tooth;

k) injection into the pleural cavity in the case of pleuritic complaints l) instillation into the intestines in the case of intestinal complaints, especially in the case of ulcerous colitis, Crohn's disease or anal fissures.

In particular, the use of resiniferatoxin (RTX) is proposed for preparing an agent for the local treatment of pain conditions, namely:

- postoperative pain conditions
- arthritis
- local wound pain after surgery in the form of a flushing solution for intraoperative application for open or arthroscopic or endoscopic surgery, including liposuction;
  - joint pain
  - bone pain after osteotomy
  - frozen shoulder local wound pain after surgery in the form of a flushing solution for intraoperative application for open or arthroscopic or endoscopic surgery, including liposuction;

local treatment of joint pain by intraarticular injection in the case of
arthrosis
rheumatoid arthritis
infectious arthritis
chondrocalcinosis
ligamentary damage
meniscus lesion
cartilage damage
synovitis
arthrofibrosis
Sudeck's disease
necrosis of portions of a joint
neuropathic joint pain Local treatment of bone pain after bone surgery by application on the bone, for example, after
iliac crest osteotomy
Hallux-Valgus correction Treatment of bone pain by injection into the bone
in the case of necrosis of the head of the femur into the latter into the body of a vertebra in the case of osteochondrosis;

Local treatment of joint stiffness, especially in the case of arthrofibrosis or a frozen shoulder;

Local treatment of muscle pain by intramuscular injection, preferably if there is a tear in muscle fibers, if there is pain after muscular exertion or in the case of spastic diseases;

Local injection into the painful meniscus, if there is degeneration of or a tear in the meniscus;

Treatment of back pain by injection into the intervertebral disk in the case of the degeneration of or a tear in the intervertebral disk;

Injection about a painful nerve, especially trigeminus neuralgia, neurinoma, Morton neurinoma, phantom pain or scar neurinoma;

Treatment of toothache by local intradental or peridental administration in the case of: dental caries
all forms of toothache
before, during or after tooth extraction
before, during or after a tooth implanting
topical administration in the case of parodontitis
topical administration in the case of an exposed neck of a tooth;

Injection into the pleural cavity in the case of pleuritic complaints.

The concentration of RTX advisably is between 100 nmolar and 10 µmolar and preferably between 500 nmolar and 1 µmolar.

Preferably, the agent does not contain any alcohol and especially not any ethanol. Ethanol has the disadvantage that it can bring about a local inflammation and lead to painful neuritis.

In a preferred embodiment of the invention, an x-ray contrasting agent, preferably substances containing gadolinium, iodine or barium, such as a barium addition or an MRI contrasting agent are used in addition to the RTX, so that an imaging control of the distribution of the RTX in the intracapsular space is possible. Depending on the method, the following substances can be used as contrasting agents:

X-ray, CT: Iodine-containing substances, such as triodinated benzoates or Iopamidol, ideally 30-80 g/100 mL or, for example, 10% of a different contrasting agent, such as barium MRI: For example, gadolinium, for example, 469.01 mg of gadopentate dimeglumide, 0.99 mg of meglumin, 0.4 mg of dimethylenetriamine pentaacetate per 1 mL.

For a further embodiment, an antibiotic, disinfecting and/or sterilizing substance is additionally added to the RTX.

For a further embodiment, a viscous additive, such as hyaluronic acid, preferably in a concentration of 0.1-10 mg/milliliter of injections solution, is used in addition to the RTX. This leads to an improvement in the mechanical sliding of the joint.

For a further embodiment, a vasoconstrictor, preferably adrenaline, noradrenaline, phenylephrin or ornipressin or other, similar, preferably alpha-adrenergic vasoconstrictors are used in addition to the RTX. With adrenaline, the total dose of neurotoxin (that is, of the substance toxic for the peripheral nervous system) can be increased by the factor of 2, since the systemic action is reduced by the decreased absorption. The adrenaline concentration may amount to 1:10,000 to 1 80,000 to 1 200,000. The total dose of adrenaline is less than 0.25 mg. A 50 mL solution of 1:200,000 adrenaline contains 0.25 mg of adrenaline.

For a further embodiment, glycerin is used as solvent in addition to the RTX. Glycerin also has neurotoxic properties (especially, however, if it is injected intraneurally). Moreover, glycerin can lubricate the joint, so that there is also a physical effect here. The concentration of glycerin preferably is between 10 and 95%. Instead of glycerin, water, a salt solution, sodium iothalamates, iophenylate, ricin, polyethylene glycol or polypropylene glycol may be used as solvent medium. As a solvent, glycerin has the advantage that it is hyperbaric and, in itself, also already somewhat neurotoxic.

For a further embodiment, a steroid is used in addition to the RTX, in order to control any inflammatory reaction, which may occur. With this, moreover, a causal treatment of painful, inflammatory joint diseases, which supports the symptomatic, neurolytic treatment, can be added more readily. Betamethasone has proven to be particularly suitable, for example, in the form of 5 mg of betamethasone as dipropionate (crystalline suspension) and 2 mg of betamethasone as disodium phosphate (solution in 1 mL can be added to the total amount that is to be injected). This solution is equivalent to 45/23 mg of prednisone/prednisolone.

Preferably, the agent is used for denervation or neurolysis in degeneratively diseased joints.

The agent may be dissolved in a carrier liquid (carrier), a pharmacologically acceptable vehicle, especially from the group of sodium chloride injection solution, Ringer's injections solution, isotonic dextrose, sterile water, lactated Ringer's injections solution, distilled water or mixtures thereof, for local injection.

The agent may contain additionally a permeation-promoting substance, such as ethoxyethylene diglycol, purified phosphatidyl cholines, propylene glycol dipelargonates (DPPG) or with glycosylated, ethoxylated glycerides.

The agent may also contain additionally a substance, preferably glucosamininoglycans or hyaluronic acid, which enables the release of the RTX to be retarded or prolonged.

For a further embodiment, a different pH is produced at the site of action, preferably by mixing RTX with a suitably buffered medium. A different activity profile can be produced by shifting the pH. The effect of RTX is enhanced at a pH below 7.4 and the painfulness of the injection is reduced clearly at a pH above 7.4.

Advisably, the mixture is dissolved in a buffer solution with a pH above 7.6 and preferably above 8.5. Alternatively, the agent may be dissolved in a buffer solution with a pH below 7.2 and preferably below 6.5.

For a further embodiment, therefore, the pH at first is adjusted to a value higher than 7.4 for the application or injection by means of suitable buffer media, which can also be released with delay by microencapsulation or in solid form, for example, as a powder or as an implant, such as a bone-replacement material. Subsequently, the pH drops, preferably within minutes to hours, to a value below 7.4. Instead of glycerin, water, salt solution, sodium Iothalamate, iophenylate, ricin, polyethylene glycol or polypropylene glycol can be used as solvent. As solvent, glycerin has the advantage that it is hyperbaric and also already somewhat neurotoxic.

For a further embodiment, calcium Ca2+ or comparable ions are used in a solvent in addition to RTX at a concentration, higher than that physiologically present and are released simultaneously or with delay. Calcium is necessary for the action of RTX and improves the effect of the latter if present at a concentration above the physiological one. Preferably, the concentration of calcium exceeds 2 mmolar and particularly 4 mmolar. Some materials have also proven to enhance the effect of RTX, for example, magnesium, antioxidants, preservatives and excipients, especially sodium bisulfite (>0.2%), NaHSO3, ammonium compounds, such as ammonium sulfate (NH4)2SO4, 2-10 (–30%) and polysorbate 80 (PS80) 0.025 mg/milliliter.

The concentration of salts and ions, dissolved in the solution medium, preferably is higher than the normal physiological concentration (for example, in Ringer lactate).

Preferably, RTX is dissolved in a solvent, which is compatible with the body, and advisably is injected in an amount, which corresponds to the available space in the joint, which is to be treated, so that this space is filled barely to firmly. With that, the advantage of an optimum local distribution of the RTX is achieved. It is, however, also possible to inject less liquid. In that case, however, the joint must be moved well in order to improve the distribution of the substance combination.

The liquid volume, to be injected into the intracapsular region, may vary from 0.1 to 150 mL. For a finger joint, a maximum of about 1 mL is sufficient, for the shoulder joint, a maximum of 10 mL, for the knee joint, a maximum of 30 to 50 mL and preferably of not more than 2 mL.

The dosage of the combination of substances depends on the localization and indication.

The dosage of RTX depends on the absolute solubility of the latter in the solution medium selected. The thickness of the capsule of the joint affected has a decisive effect on the dosage. The thicker the capsule, the higher is the concentration or amount of RTX, which is required.

The method for treating pain with the agent, used pursuant to the invention, consists therein that resiniferatoxin (RTX) is dissolved in a suitable solvent, which is compatible with the body, and a volume, preferably of 0.12150 mL, thereof a) is injected locally into the pain-affected tissues structure of the patient or b) is allowed to drip locally on to the surgical wound or c) injected locally into the intracapsular region or d) injected locally into the capsule of a joint affected by pain.

The nociceptive nerve fibers are made insensitive to pain by the resiniferatoxin (RTX) for at least 14 days and preferably for at least 8 weeks. The resiniferatoxin (RTX) is used advantageously at such a concentration, that neurolysis occurs. The concentration of RTX advisably is between approximately 10 nmolar (nM) and 100 μmolar (μM).

The method, described above, is suitable especially for the following indications:

- for local wound pain after surgery in the form of a flushing solution for intraoperative application for open or arthroscopic or endoscopic surgery, including liposuction;
- local treatment of joint pain by intraarticular injection in the case of
  - arthrosis
  - rheumatoid arthritis
  - infectious arthritis
  - chondrocalcinosis
  - ligamentary damage
  - meniscus lesion
  - cartilage damage
  - synovitis
  - arthrofibrosis
  - Sudeck's disease
  - necrosis of portions of a joint
  - neuropathic joint pain
- Local treatment of bone pain after bone surgery by application on the bone, for example, after iliac crest osteotomy or Hallux-Valgus correction
- Treatment of bone pain by injection into the bone in the case of necrosis of the head of the femur into the head of the femur into the body of a vertebra in the case of osteochondrosis;
- Local treatment of joint stiffness, especially in the case of arthrofibrosis or a frozen shoulder;
- Local treatment of muscle pain by intramuscular injection, preferably if there is a tear in muscle fibers, if there is pain after muscular exertion or in the case of spastic diseases;
- Local injection into the painful meniscus, if there is degeneration of or a tear in the meniscus;
- Treatment of back pain by injection into the intervertebral disk in the case of the degeneration of or a tear in the intervertebral disk;
- Injection about a painful nerve, preferably in the case of trigeminus neuralgia, neurinoma, Morton neurinoma, phantom pain or scar neurinoma;
- Treatment of toothache by local intradental or peridental administration in the case of: dental caries
  - all forms of toothache
  - before, during or after tooth extraction
  - before, during or after a tooth implanting
  - topical administration in the case of parodontitis
  - topical administration in the case of an exposed neck of a tooth;
- Injection into the pleural cavity in the case of pleuritic complaints
- Instillation into the intestines in the case of intestinal complaints, especially in the case of ulcerous colitis, Crohn's disease or anal fissures.

The advantage of this method consists therein that it permits local administration without a local anesthetic. As a result, a lower concentration of RTX is possible, so that fewer local side effects of RTX, such as swelling or inflammation, arise.

For a special embodiment, the agent is injected into a synovial cavity, which is not lined with urothel. The injection into a synovial cavity has proven to be particularly advantageous, because an optimum residence time for developing the effect is achieved here in combination with minimum side effects, such as inflammation or pain.

The invention is implemented in greater detail in the following by means of numerous examples.

Example 1

Under the optionally simultaneous (image converter, CT, sonography, MRI, etc.) or subsequent (x-ray, CT, MRI, sonography, arthroscopy, etc.) imaging control, the therapist brought an injection needle into the joint space of a knee joint and injected 9 mL of a 500 nmolar solution (approximately 0.003 mg) of resiniferatoxin into the intracapsular space. The patient noted a clear alleviation of his symptoms already 14 hours after the intervention. This alleviation lasted for more than 6 months.

Example 2

Under the optionally simultaneous (image converter, CT, sonography, MRI, arthroscopy, etc.) or subsequent (x-ray, CT, MRI, sonography, etc.) imaging control, the therapist brought an injection needle into the joint space of a knee joint and injected 20 mL of a 500 nmolar solution (approximately 0.006 mg) of resiniferatoxin into the intracapsular space. The patient noted a clear alleviation of his symptoms already a few days after the intervention. This alleviation lasted for more than 6 months.

Example 3

The injected solution corresponded to that of Example 1 with the difference that, for the imaging method to be used, 5 mL of a visible contrasting agent (Iopamidol) was added at a concentration of 50 g/100 mL. After the injection, this contrasting agent spread out within the joint capsule and documented the position of the injection needle and the distribution of the RTX within the joint capsule. The injected solution, containing RTX, was drawn off again directly after the injection. It could, however, also be drawn off after a defined, substance-dependent time of action or not be drawn off at all. The patient noted a clear alleviation of his symptoms already 15 hours after the intervention. This alleviation lasted for more than 8 months.

Example 4

The therapist placed a thin infusion catheter, similar to an epidural catheter, into the affected joint and, with a perfuser, injected a solution of 1 liter of 100 nmolar of resiniferatoxin into the affected joint at a rate of 1-10 mL/h for 12 hours. Optionally, he also placed a drainage catheter with an optionally defined drainage resistance (such as 20 mm Hg), in order to achieve a liquid turnover. With this method, the therapist achieved a uniform infiltration of the painful joint, without large concentration peaks. Moreover, it was possible to define the period of action better.

During subsequent arthroscopies after 1, 2, 7, 14 and 28 days, it was possible to show that only a very little inflamed tissue was present. The patient noted a clear alleviation of his symptoms already 12 hours after the intervention. This alleviation lasted for more than 1 year.

Example 5

After a knee joint prosthesis had been implanted, the therapist injected 50 mL of a solution of 100 nmolar (approximately 0.001 mg) solution of resiniferatoxin into the joint capsule, which had been closed off once again. It was possible to minimize postoperative pain by these means.

Example 6

After a hip joint prosthesis had been implanted, the therapist injected 50 mL of a solution of 100 nmolar (approximately 0.001 mg) solution of resiniferatoxin into the periprosthetic region without a capsule. It was possible to minimize postoperative pain by these means.

Example 7

A solution of 5 μmolar (approximately 0.03 mg) solution of resiniferatoxin was injected into the (neo)-capsule about the prosthesis of a patient with a painful, septic loosening of a total hip endoprosthesis. Subsequently, the patient experienced a permanent (more than one year) alleviation of pain within a few (6-12) hours. In addition, the infection about the prosthesis was brought very much under control by the diffusion of the RTX (which also had antiseptic activity) along the shaft of the prosthesis and about the socket and, in some cases, was even eliminated completely. Optionally, this treatment may be supported with systemically administered antibiotics (such as 450 mg of Rifampicin, 750 mg of ciproflaxacin). It was possible to show radiologically that the bone substance had consolidated about the prosthesis.

Example 8

Under the optionally simultaneous (image converter, CT, sonography, MRI, etc.) or subsequent (x-ray, CT, MRI, sonography, arthroscopy, etc.) imaging control, the therapist brought an injection needle into the joint space of a knee joint and injected 9 mL of a 500 nM (approx. 0.003 mg) solution of resiniferatoxin, buffered with a buffer to a pH of 8.5, together physiological salt solution into the intracapsular space. The patient noted a clear alleviation of his symptoms already a few minutes after the intervention. This alleviation lasted for more than 6 months.

Example 9

Under the optionally simultaneous (image converter, CT, sonography, MRI, etc.) or subsequent (x-ray, CT, MRI, sonography, arthroscopy, etc.) imaging control, the therapist, brought an injection needle into the joint space of a knee joint and injected 9 mL of a 500 nmolar solution (approximately 0.003 mg) of resiniferatoxin, buffered to a pH of 6.5 with a buffer, together with a physiological salt solution into the intracapsular space. Within minutes of the intervention, the patient already noted a clear alleviation of his symptoms, which lasted for more than 6 months.

Example 10

Under the optionally simultaneous (image converter, CT, sonography, MRI, etc.) or subsequent (x-ray, CT, MRI, sonography, arthroscopy, etc.) imaging control, the therapist, brought an injection needle into the joint space of a knee joint and injected 9 mL of a 500 nmolar solution (approximately 0.003 mg) of resiniferatoxin, in a physiological Ringer solution with 10 mmolar Ca2+ into the intracapsular space. Within minutes of the intervention, the patient already noted a clear alleviation of his symptoms, which lasted for more than 6 months.

Example 11

The shoulder joint of a patient with painful capsulitis of joints (frozen shoulder) was injected with 9 mL of a 100 nmolar (approximately 0.001 mg) solution of resiniferatoxin in physiological salt solution. Once again, it was possible to check the distribution of the substance by adding the appropriate contrasting agent and employing an imaging procedure. Optionally, a substance with antiphlogistic activity was admixed. A few minutes after the injection, the pain was alleviated permanently, so that the patient was able to regain the mobility, lost due to capsulitis, by undergoing physiotherapy. For this application, only a temporary analgesia (2-3 weeks) is desired. For this reason, the concentration of the neurotoxic substances, if anything, was kept low.

Example 12

The shoulder joint of a patient with painful capsulitis of joints (frozen shoulder) was injected with 3 mL of a 500 nmolar (approximately 0.001 mg) solution of resiniferatoxin in physiological salt solution. A few minutes after the injection, the pain had abated permanently, so that the patient, with physiotherapy, regained the mobility lost due to capsulitis.

Example 13

The therapist injected 5 mL of a solution of a 500 nmolar (approximately 0.001 mg) solution of resiniferatoxin, buffered to a pH of 8.5 with a buffer, together with physiological salt solution as solvent, into a chronically inflamed bursa (Bursa trochenterica) over the greater trochanter of the hip. Within 60 minutes, the symptoms of the patient disappeared and the patient remained asymptomatic at this place for several years.

Example 14

The therapist injected 50 mL of a 100 nmolar (approximately 0.001 mg) solution of resiniferatoxin in glycerin or Ringer lactate as solvent. Within 60 minutes, the symptoms of the patient disappeared and the patient remained asymptomatic at this place for several years.

The invention claimed is:

1. A method for treating a joint affected by pain, the method comprising injecting an agent comprising resiniferatoxin and a calcium salt dissolved in a physiologically suitable solvent locally into the intracapsular region or the bursa of the joint affected by pain, wherein the concentration of resiniferatoxin in the agent is between approximately 10 nmolar (nM) and 100 μmolar (μM), wherein the agent has a calcium ion concentration of greater than 2 mmolar, and wherein the agent is dissolved in a buffer solution with a pH higher than 7.6 wherein the concentration of resiniferatoxin (RTX) in the agent is such that neurolysis occurs to nociceptive nerve fibers in the joint, and wherein nociceptive nerve fibers in the joint are made insensitive to pain for a period of at least 14 days after the agent is injected into the intracapsular region or the bursa of the joint affected by pain.

2. The method according to claim 1 further comprising drawing out at least a portion of the agent that has been injected locally into the intracapsular region or the bursa of the joint affected by pain.

3. The method according to claim 1 wherein the joint is selected from the group consisting of a human knee joint, a human hip joint, a human shoulder joint and a human finger joint.

4. The method according to claim 1 wherein the physiologically suitable solvent is glycerin.

5. The method according to claim 1 wherein the agent does not contain any local anesthetics.

6. The method according to claim 1 wherein the agent does not contain any ethanol.

7. The method according to claim 1 wherein the agent further comprises a permeation promoter selected from the following group consisting of dimethyl sulfoxide, ethoxyethylene diglycol, phosphatidyl cholines, propylene glycol dipelargonates and glycosylated ethoxylated glycerides.

8. The method according to claim 1 wherein the agent does not contain any other pharmacologically active substances.

9. The method according to claim 1 wherein the agent further comprises an x-ray contrasting agent and/or an MRI contrasting agent.

10. The method according to claim 1 wherein the agent further comprises a steroid.

11. The method according to claim 1 wherein the agent further comprises a vasoconstrictor.

12. The method according to claim 1 wherein the agent further comprises glucosaminoglycans or hyaluronic acid.

13. The method according to claim 1 wherein a volume of the agent is injected into the intracapsular region or the bursa of the joint affected by pain using an infusion catheter over time and wherein a drainage catheter is also placed into the intracapsular region or the bursa of the joint affected by pain during the injection in order to achieve a liquid turnover.

14. The method according to claim 1 wherein the agent is injected into the intracapsular region or the bursa of the joint affected by pain in an amount sufficient to fill the available space in the joint.

* * * * *